(12) United States Patent
Somberg et al.

(10) Patent No.: US 8,481,600 B2
(45) Date of Patent: Jul. 9, 2013

(54) FORMULATION OF ASPIRIN THAT IS STABLE AND SHOWING MINIMAL HYDROLYSIS FOR PARENTERAL ADMINISTRATION FOR THE TREATMENT OF CARDIOVASCULAR AND OTHER DISEASE STATES

(75) Inventors: John Charin Somberg, Lake Forest, IL (US); Vasant V Ranade, Libertyville, IL (US)

(73) Assignee: Academic Pharmaceuticals, Inc., Lake Bluff, IL (US)

( * ) Notice: Subject to any disclaimer, the term of this patent is extended or adjusted under 35 U.S.C. 154(b) by 593 days.

(21) Appl. No.: 12/454,847

(22) Filed: May 26, 2009

(65) Prior Publication Data

US 2010/0173875 A1 Jul. 8, 2010

Related U.S. Application Data

(63) Continuation of application No. 11/803,619, filed on May 16, 2007, now abandoned.

(51) Int. Cl.
*A01N 31/14* (2006.01)
*A61K 31/075* (2006.01)

(52) U.S. Cl.
USPC .......................................... 514/718; 514/715

(58) Field of Classification Search
None
See application file for complete search history.

(56) References Cited

U.S. PATENT DOCUMENTS 3,654,308 A * 4/1972 Szmuszkovicz .............. 548/510

* cited by examiner

*Primary Examiner* — Jeffrey S. Lundgren
*Assistant Examiner* — Meghan Finn
(74) *Attorney, Agent, or Firm* — Vance Intellectual Property, PC (57) ABSTRACT

Disclosed herein are ways to solubilize aspirin for parenteral administration containing aspirin and a diluent NNDMA (N,N-Dimethylacetamide) useful in the treatment of acute coronary syndromes as well as other disease states. The solution so constituted is stable at room temperature for prolonged periods without decomposition and avoids significant hydrolysis of the aspirin and thus the loss of the anti-platelet action when stored.

7 Claims, 6 Drawing Sheets

Fig. 1  HPLC chromatogram of Aspirin.

Fig. 2. HPLC chromatogram of Aspirin in glycerin, propranolol and Tween 80.

Fig. 3. Chromatogram of Aspirin dissolved in NNDMA stored at room temperature for six months.

Fig. 4. Chromatogram of Aspirin dissolved in NNDMA and stored at 40°C for 6 months.

Fig. 5. Chromatogram of Aspirin dissolved in NNDMA, glycerol and Tween 20.

Fig. 6. Chromatogram of Aspirin in NNDMA diluted in distilled water and glucose(D5W) after 12 hours.

FORMULATION OF ASPIRIN THAT IS STABLE AND SHOWING MINIMAL HYDROLYSIS FOR PARENTERAL ADMINISTRATION FOR THE TREATMENT OF CARDIOVASCULAR AND OTHER DISEASE STATES

This application is a continuation in part of application Ser. No. 11/803,619 first filed on May 16, 2007.

BACKGROUND OF THE INVENTION

Cardiovascular disease is the leading cause of death in the United States and in most developed countries. Long-term aspirin therapy reduces the risk of subsequent myocardial infarction (MI), stroke and vascular death among patients with a wide range of prior manifestations of cardiovascular disease. Aspirin is effective in the prevention of coronary artery disease (CAD) and stroke and thus can be used as a primary prevention of CAD. Among patients with prior MI, stroke, transient ischemic attacks (TIAs), unstable angina, angioplasty and acute coronary syndromes, immediate aspirin therapy provides significant benefit in reducing death, recurrent MI, TIA's or stroke. The benefits are seen in men and women, the elderly of both sexes as well as patients with risk factors for CAD, hypertension and diabetes.

The most widely employed dose of ASA in primary as well as the secondary prevention trials is a dose of 325 mg/day. Dosages in a range of 75 to 325 mg per/day have been found effective in clinical trials. The survival benefits of immediate oral aspirin therapy for an acute MI or stroke are seen during the first month and persist for several years. Oral ASA therapy though has limitations. It cannot be given to intubated patients, has slow onset of action, and in emergency, is often given to a patient to chew with the potential of GI upset leading to emesis or a severe burning of the oral mucosa and upper esophagus. Efforts have been made to develop a parenteral formulation of aspirin. Aspirin has poor solubility in water at 25° C. In an attempt to prepare an aqueous formulation of aspirin, aspirin was converted to its lysine salt. Lysine acetylsalicylate (trade name Aspegic or Aspisol) is the lysine salt of aspirin and is readily water soluble and this compound has been used as an injectable form of aspirin in Europe. However, a considerably larger dose is needed to be given, since it was found that 900 mg of lysine salt of aspirin is approximately equivalent to 500 mg of aspirin. This salt of ASA needs to be metabolized to salicylic acid for its biologic actions. The drug is delivered to target organs, where aspirin is released for its pharmacological effects. Studies with this formulation suggested that the lysine salt was effective in the treatment of acute migraine headaches. The shortest half life after IV administration was 7.5 minutes. Metabolism and hydrolysis to salicylic acid is rapid. Limiting the utility of the lysine ASA is the sensitivity it can cause that can lead to anaphylactic shock in patients with an incidence of up to 5%. This adversity limits the utility of the lysine ASA preparation for clinical use.

PRIOR ART

Many attempts have been made to prepare ASA for IV administration with varying degrees of success.

For example, U.S. Pat. No. 3,985,792 teaches that the sodium acetylsalicylate is made by reacting ASA with sodium bicarbonate in water isolating the crystalline dehydrate and removing the water of hydration from the di-hydrate to produce anhydrous sodium acetylsalicylate. This material needs to be re-hydrated for administration and is subject to decomposition during storage and re-construction. Other methods have been developed to resist the decomposition, but the material still needs to be dissolved before administration (Galat, Int Pub No WO 00/02565).

A number of strategies have been proposed to maintain a soluble solution. One strategy has been to prepare a soluble salt of aspirin. One approach has been the formation of an ornithine acetylsalicylate (British Patent #883,331); a glycerol acetylsalicylate (U.S. Pat. No. 3,644,424), a glucamine or meglumine salt of acetylsalicylic acid (U.S. Pat. No. 4,748,174) or lysine salts (U.S. Pat. Nos. 4,885,287 or 4,265,888). These strategies have the drawback of producing salts that may have unpredicted side effects such as the problems of the lysine salt causing anaphylaxis.

Other strategies to prepare a solution for IV administration have been to make a granular potassium bicarbonate solution (U.S. Pat. No. 5,723,453), producing an alkaline diphosphate compound(s) (U.S. Pat. No. 4,275,059) or a composition containing ascorbic acid or its derivatives and aspirin for IV administration (U.S. Pat. No. 5,128,334). These strategies have the drawback of producing very basic or very acidic solutions that could cause phlebitis at the administration site and/or thrombosis.

SUMMARY OF THE INVENTION

The present invention relates to the preparation of a solution of aspirin the formulation of which utilise a diluent NNDMA (N,N-Dimethylacetamide). The formulation is used for the treatment of emergency ischemic conditions, including acute coronary syndrome, myocardial infarction and acute neurologic ischemic conditions.

DETAILED DESCRIPTION OF THE INVENTION

The findings reported herein deal with the novel preparation of an aspirin formulation that does not utilize a pro-drug strategy or the making of a salt of aspirin for administration. Initially we tried several buffers, solubilizers at different pH conditions and concentrations. While ASA can be solubilized in a number of buffers and solutions this material readily hydrolyzes. Hydrolysis reduces the effectiveness of aspirin by decreasing its binding to platelets and thus a preparation was sought that reduced ASA hydrolysis. Our results indicate that aspirin is readily soluble in N,N-dimethylacetamide and is stable at a concentration of up to 500 mg/ml without undergoing significant hydrolysis even when stored at 40° C. for up to 6 months. N,N-dimethylacetamide (NNDMA) is considered a safe solvent by being on the list of approved products for parenteral products developed by the Food and Drug Administration. We present a unique method for preparation of a soluble solution of aspirin. The results of stability, purity and recovery following high pressure liquid chromatography analysis of this formulation are described in the following pages, tables and figures.

Solubility and Stability of ASA in a Number of Solvent Systems:

Specifically the present invention provides parenteral solutions suitable for intravenous administration containing aspirin as an active ingredient. The invention provides solutions having extended stability that are suitable for parenteral administration comprising aspirin in buffers having a pH from 1.5 to 6.8. Also included within the scope of the invention are methods for producing such solutions. Further the invention provides solutions suitable for parenteral administration for treating patients with prior MI, stroke, unstable angina, TIA's, acute coronary syndromes and in patients who have undergone angioplasty and coronary stenting. The parenteral, aspirin therapy may provide significant benefits in reducing death, recurrent MI or stroke in patients.

Parenteral solutions comprising aspirin in buffers are typically prepared by mixing the required amount of aspirin in the buffer. The process is preferably carried out at room temperature, although other temperatures are acceptable for these preparations. Several buffers with different molarities were tried for dissolution of aspirin, however, remarkably it was found that the use of NN-dimethylacetamide (NNDMA) as a solvent, resulted in clear solutions that were stable when stored at room temperature and 40° C. over a period of 6 months without the formation of turbidity or a precipitate and without significant hydrolysis of aspirin.

Formulation Development of ASA in NNDMA

ASA (aspirin) was attempted to be dissolved in a number of solvent systems and then stability was determined if these solutions provided clear, colorless dissolution of ASA. In the following buffers aspirin was found riot to be soluble. These buffers are listed below:
1. Dissolution of aspirin in a concentration ranging from 10 mg/ml to 50 mg/ml in 10 ml of bis-tris buffer 10.05M) resulted in a suspension that was not clear even at a 10 mg/ml concentration level.
2. Dissolution of aspirin in a concentration ranging from 10 mg/ml to 50 mg/ml in 10 ml of CAPS buffer (0.05M) resulted in a suspension that was not clear even at a 10 mg/ml concentration level.
3. Dissolution of aspirin in a concentration ranging from 10 mg/ml to 50 mg/ml in 10 ml of TAPS buffer (0.05M) resulted in a suspension that was not clear even at a 10 mg/ml concentration level.
4. Dissolution of aspirin in a concentration ranging from 10 mg/ml to 50 mg/ml in 10 ml of HEPES buffer (0.05M) resulted in a suspension that was not clear even at a 10 mg/ml concentration level.
5. Dissolution of aspirin in a concentration ranging from 10 mg/ml to 50 mg/ml in 10 ml of AMPSO buffer (0.05M) resulted in a suspension that was not clear even at a 10 mg/ml concentration level.
6. Dissolution of aspirin in a concentration ranging from 10 mg/ml to 50 mg/ml in 10 ml of sodium acetate (pH 6.5 and 3.8) buffer (0.1M) resulted in a suspension that was not clear even at a 10 mg/ml concentration level.
7. Dissolution of aspirin in a concentration ranging from 10 mg/ml to 50 mg/ml in 10 ml of Tricine buffer (0.1M) resulted in a suspension that was not clear even at a 10 mg/ml concentration level.
8. Dissolution of aspirin in a concentration ranging from 10 mg/ml to 50 mg/ml in 10 ml of bicine buffer (0.1M) resulted in a suspension that was not clear even at a 10 mg/ml concentration level.
9. Dissolution of aspirin in a concentration ranging from 10 mg/ml to 50 mg/ml in 10 ml of saline (normal) buffer (0.1M) resulted in a suspension that was not clear even at a 10 mg/ml concentration level.
10. Dissolution of aspirin in a concentration ranging from 10 mg/ml to 50 mg/ml in 10 ml of bis-tris buffer (0.1M) resulted in a suspension that was not clear even at a 10 mg/ml concentration level.
11. Dissolution of aspirin in a concentration ranging from 10 mg/ml to 50 mg/ml in 10 ml of CAPS buffer (0.1M) resulted in a suspension that was not clear even at a 10 mg/ml concentration level.
12. Dissolution of aspirin in a concentration ranging from 10 mg/ml to 50 mg/ml in 10 ml of TAPS buffer (0.1M) resulted in a suspension that was not clear even at a 10 mg/ml concentration level.
13. Dissolution of aspirin in a concentration ranging from 10 mg/ml to 50 mg/ml in 10 ml HEPES buffer (0.1M) resulted in a suspension that was not clear even at a 10 mg/ml concentration level.
14. Dissolution of aspirin in a concentration ranging from 10 mg/ml to 50 mg/ml in 10 ml of AMPSO buffer (0.1M) resulted in a suspension that was not clear even at 10 mg/ml concentration level.
15. Dissolution of aspirin in a concentration ranging from 10 mg/ml to 50 mg/ml in 10 ml of sodium acetate pH 6.5 and 3.8) buffer (0.1M) resulted in a suspension that was not clear even at a 10 mg/ml concentration level.
16. Dissolution of aspirin in a concentration ranging from 10 mg/ml to 50 mg/ml in 10 ml of Tricine buffer (0.1M) resulted in a suspension that was not clear even at a 10 mg/ml concentration level.
17. Dissolution of aspirin in a concentration ranging from 10 mg/ml to 50 mg/ml in 10 ml of bicine buffer (0.1M) resulted in a suspension that was not clear even at a 10 mg/ml concentration level.

Dissolution of aspirin in the solvents described above indicated that even at a concentration level as low as 10 mg/ml, a suspension resulted and clear solutions were not obtained. These results are listed in Table 1.

In another series of experiments, dissolution of aspirin in solvents that are listed below were attempted to provide parenteral solutions suitable for intravenous administration comprising an effective amount of aspirin. If the material shows substantial hydrolysis, the biologic activity of anti-platelet action is severely affected. These solvents resulted in solutions of ASA that were found to contain, within one hour approximately 5% or more salicylic acid (hydrolysis product). Salicylic acid was found to be the only component besides aspirin that was present as a result of hydrolysis of aspirin. Typically these solutions had a concentration range of aspirin in 50-75 mg/ml. The pH of the solutions ranged from 1.5 to 6.8. Ph adjustments were made using 1N NaOH solution.

1. To water (2.0 ml), 1-propanol (0.5 ml) and Tween 20 (0.5 ml) was added to aspirin at a concentration level of up to 75 mg/ml. This resulted in a clear solution.
2. To water (2.0 ml), 1-propanol (0.5 ml) and Tween 40 (0.5 ml) was added to aspirin at a concentration level of up to 75 mg/ml. This resulted in a clear solution.
3. To water (2.0 ml), 1-propanol (0.5 ml) and Tween 60 (0.5 ml) was added to aspirin at a concentration level of up to 75 mg/ml. This resulted in a clear solution.
4. To water (2.0 ml), 1-propanol (0.5 ml) and Tween 80 (0.5 ml) was added to aspirin at a concentration level of up to 75 mg/ml. This resulted in a clear solution.
5. To water (2.0 ml), 1-propanol (0.5 ml) and PEG 300 was added to aspirin at a concentration level of up to 75 mg/ml. This resulted in a clear solution.
6. To water (2.0 ml), 1-propanol (0.5 ml) and PEG 400 was added to aspirin at a concentration level of up to 75 mg/ml. This resulted in a clear solution.
7. To water (2.0 ml), 1-propanol (0.5 ml) and PEG 600 was added to aspirin at a concentration level of up to 75 mg/ml. This resulted in a clear solution.
8. To water (2.0 ml), 1-propanol (0.5 ml) and glycerol was added to aspirin at a concentration level of up to 75 mg/ml. This resulted in a clear solution.
9. To water (2.0 ml), DMSO (1-2%) and Tween 20 was added to aspirin at a concentration level of up to 75 mg/ml. This resulted in a clear solution.
10. To water (2.0 ml), DMSO (1-2%) and Tween 40 was added to aspirin at a concentration level of up to 75 mg/ml. This resulted in a clear solution.
11. To water (2.0 ml), DMSO (1-2%) and Tween 60 was added to aspirin at a concentration level of up to 75 mg/ml. This resulted in a clear solution.
12. To water (2.0 ml), DMSO (1-2%) and Tween 80 was added to aspirin at a concentration level of up to 75 mg/ml. This resulted in a clear solution.
13. To glycerine (1 ml), 1-propanol (3 ml) and Tween 80 (0.2 ml) was added to aspirin at a concentration level of up to 75 mg/ml. This resulted in a clear solution.
14. To glycerine (1 ml), 1,2-propanol and Tween 80 (0.2 ml) was added to aspirin at a concentration level, of up to 75 mg/ml. This resulted in a clear solution.
15. To glycerine (1 ml), PEG 300 and Tween 80 (0.2 ml) was added to aspirin at a concentration of up to 75 mg/ml. This resulted in a clear solution.
16. To glycerine (1 ml), PEG 400 and Tween 80 (0.2 ml) was added to aspirin at a concentration of up to 75 mg/ml. This resulted in a clear solution.
17. To glycerine (1 ml), PEG 600 and Tween 80 (0.2 ml) was added to aspirin at a concentration of up to 75 mg/ml. This resulted in a clear solution.

Figure 1:
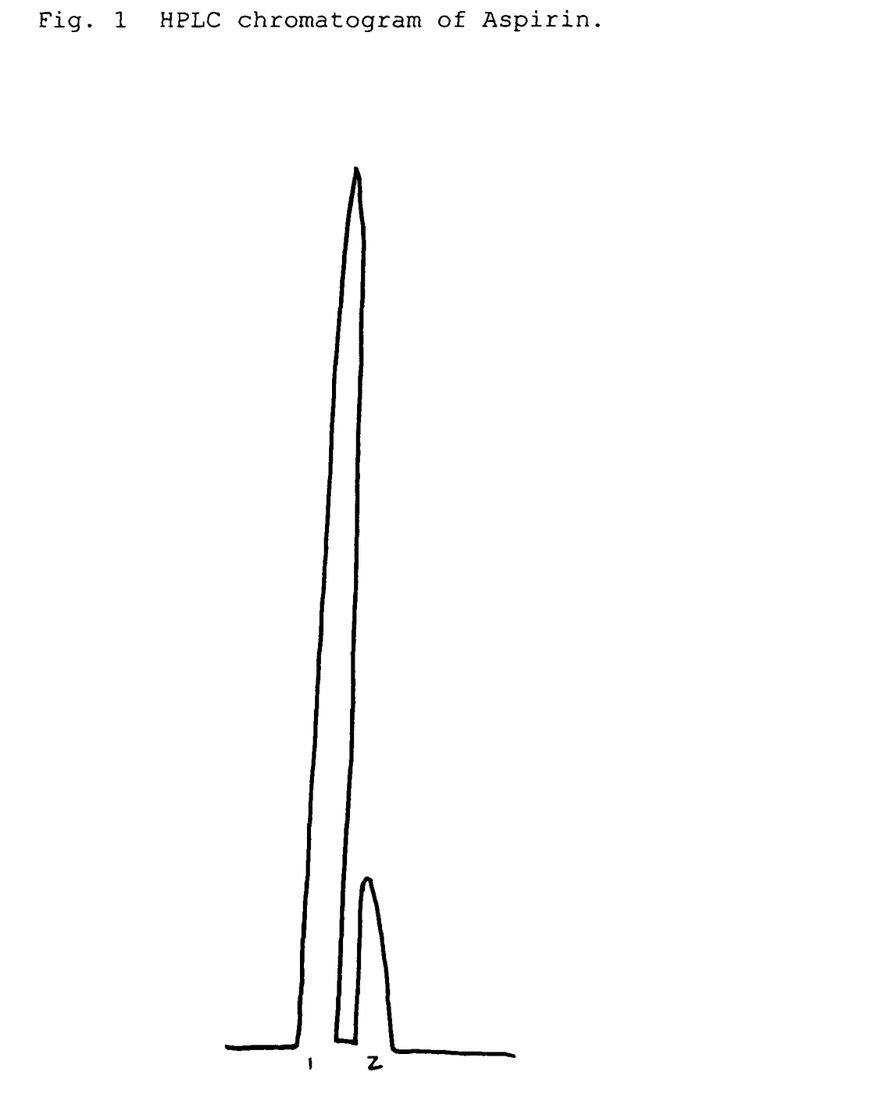
FIG. 1. HPLC (high pressure liquid chromatography) chromatogram of aspirin dissolved in water (2 ml) studied upon mixing, showing two peaks; peak 1 95.4% area and retention time of 1.25 min that is aspirin and peak 2: representing hydrolysis product, 4.9% and retention time RT of 2.74 min.
Figure 2:
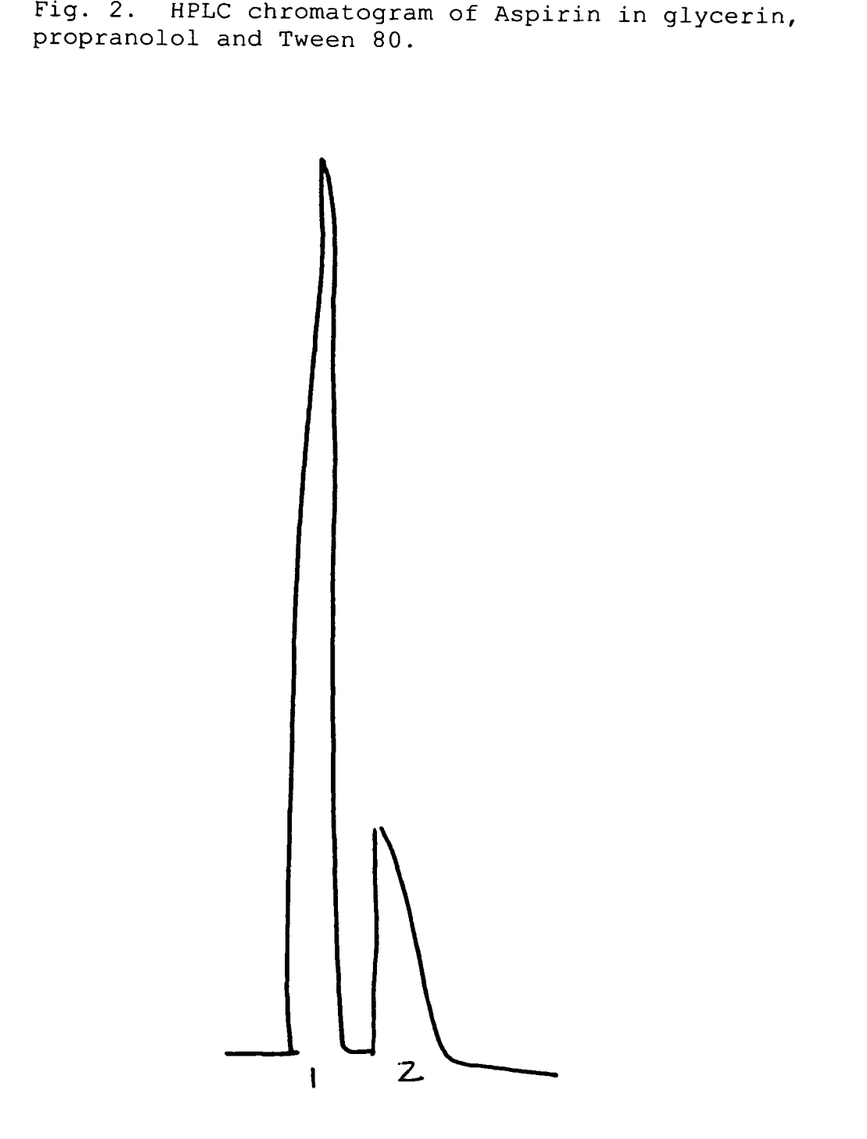
FIG. 2. HPLC of aspirin in glycerin (1 ml), 1-propanol (3 ml) and Tween 80 (0.2 ml) that shows upon mixing significant hydrolysis. Peak 1 represents 94.3% aspirin RT of 1.75 and peak 2 the hydrolysis product 5.7% at RT of 3.34.

Stability testing with these solutions indicated however that within 1 hr, approximately 5% or more of salicylic acid (hydrolysis product) was present with the above listed buffers with the remaining material being aspirin. No other decomposition product(s) were present in these solitions. (Table 2) (as an example see FIGS. 1 and 2.

Figure 3:
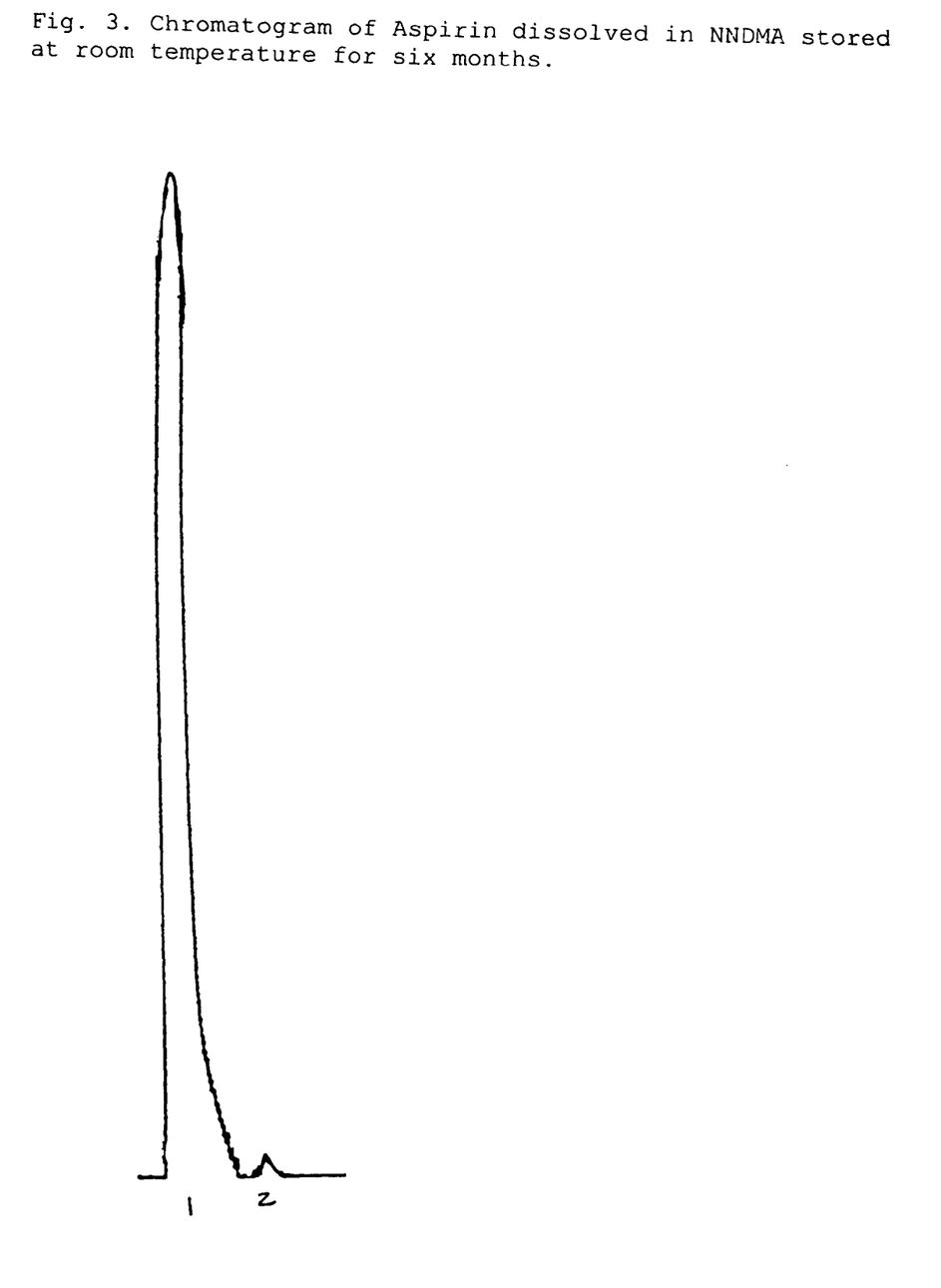
FIG. 3. HPLC of aspirin dissolved in NNDMA that is stored at room temperature for 6 months. Peak 1 shows 99.4% aspirin at RT 1.37 and a hydrolysis product of 0.3%, RT of 2.86. Despite prolonged storage there is negligible hydrolysis of the aspirin.
Figure 4:
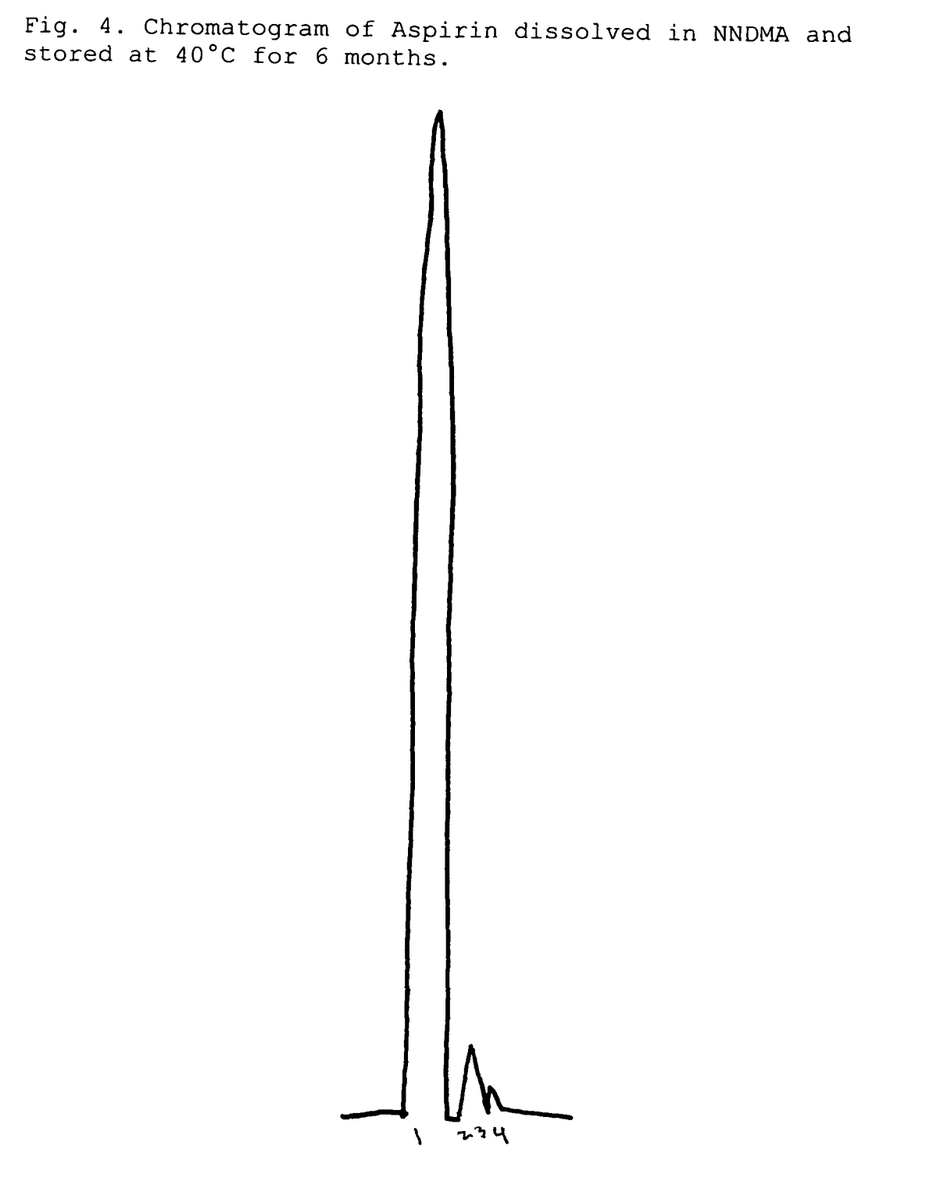
FIG. 4. HPLC chromatogram of aspirin dissolved in NNDMA and stored at 40° C. for 6 months. Peak 1 represents aspirin 98% at RT of 0.98, while peaks 2, 3 and 4 represents degradation products of 2% (RT of 1.75, 2.35 and 2.51).

In additional studies, aspirin was found to be soluble (at a concentration up to 500 mg/ml) in NNDMA (Table 3). These solutions were kept at RT and 40° C. HPLC results indicated that at RT, (up to a period of 6 months) hydrolysis was not observed; purity greater than 99% of ASA was found (FIG. 3). Solutions kept at 40° C. showed purity after a period of 6 months, with ASA purity of 97.5% and salicylic acid present as a very small hydrolysis product. (FIG. 4) The dissolution studies of ASA are summarized in Tables 3 and 4.

The dissolution studies in NNMDA and ASA at a concentration of up to 500 mg/ml are described below.

1. To N,N-Dimethylacetamide (NNDMA) (10 ml), aspirin was added at a concentration level of up to 500 mg/ml. This resulted in a clear solution.
2. To N,N-Dimethylacetamide (NNDMA) (10 ml) and ASA, glycerol (0.1 in 10 ml) added, Tween 20 (0.1 in 10 ml) were added. This resulted in a clear solution.
3. To N,N-Dimethylacetamide (NNDMA) (10 ml) and ASA, glycerol (0.1 in 10 ml), Tween 40 (0.1 in 10 ml) were added. This resulted in a clear solution.
4. To N,N-Dimethylacetamide (NNDMA) (10 ml) and ASA, glycerol (0.1 in 10 ml), Tween 60 (0.1 in 10 ml) were added. This resulted in a clear solution.
5. To N,N-Dimethylacetamide (NNDMA) (10 ml) and ASA, glycerol (0.1 in 10 ml), Tween 80 (0.1 in 10 ml) were added. This resulted in a clear solution.
6. To N,N-Dimethylacetamide (NNDMA) (10 ml) and ASA, glycerol (0.1 in 10 ml) were added. This resulted in a clear solution.
7. To N,N-Dimethylacetamide (NNDMA) (10 ml) and ASA, glycerol (0.1 in 10 ml), and DMSO (1-2%) were added. This resulted in a clear solution.
8. To N,N-Dimethylacetamide (NNDMA) (10 ml) and ASA, DMSO (1-2%) was added. This resulted in a clear solution.

Figure 5:
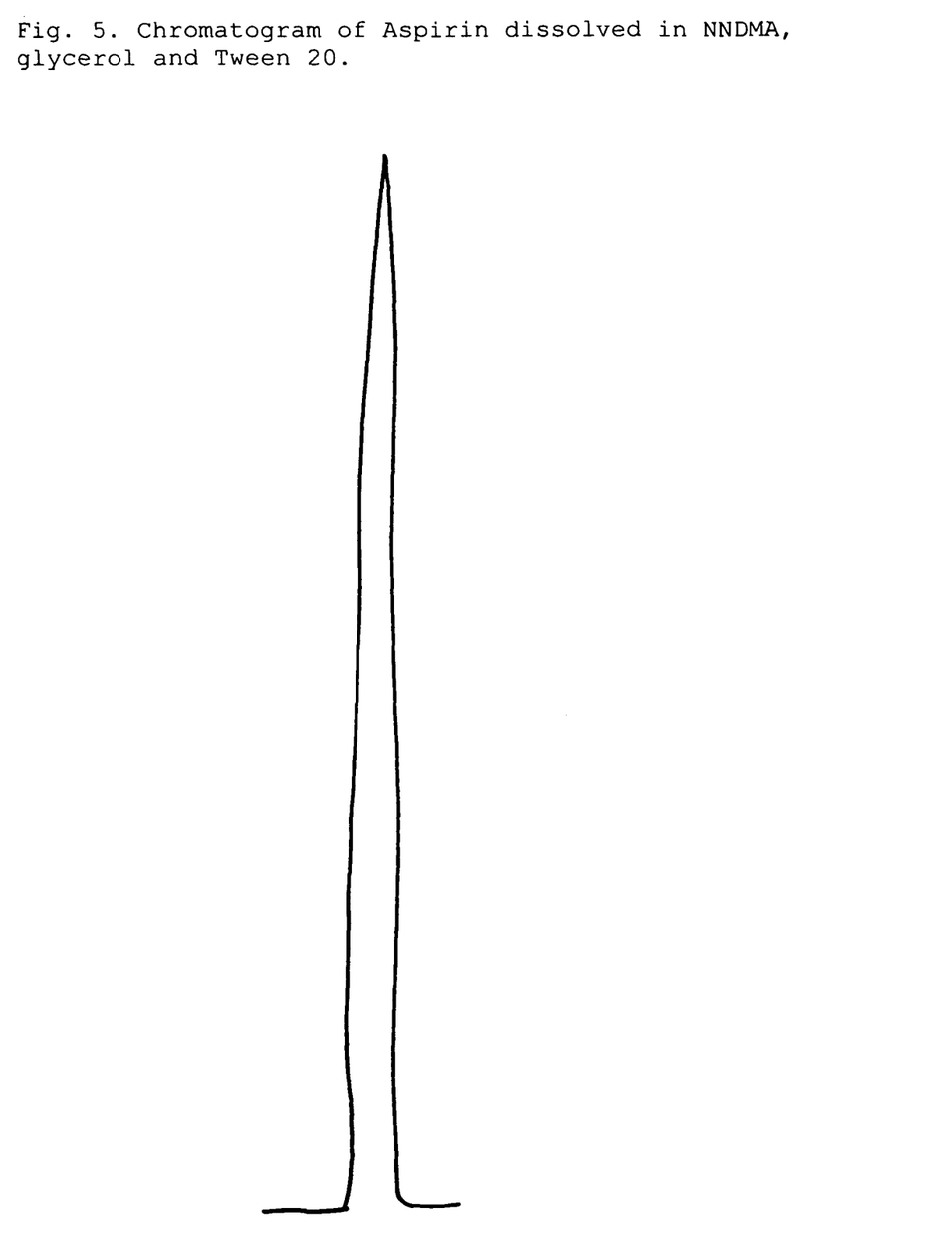
FIG. 5. HPLC chromatogram of aspirin dissolved in NNDMA, glycerol and Tween 20 kept at RT for 6 months. One peak of aspirin is seen of 99% purity at RT of 1.70, indicating essentially no hydrolysis of aspirin.

In all of these solutions, stability studies indicated that when the solution was stored at room temperature, no significant amount of hydrolysis could be detected. The amount of aspirin present was greater than 98% at room temperature for 6 months. (See FIG. 5) The pH of these solutions was adjusted in the range of 1.5-6.0 without changing solution stability.

Figure 6:
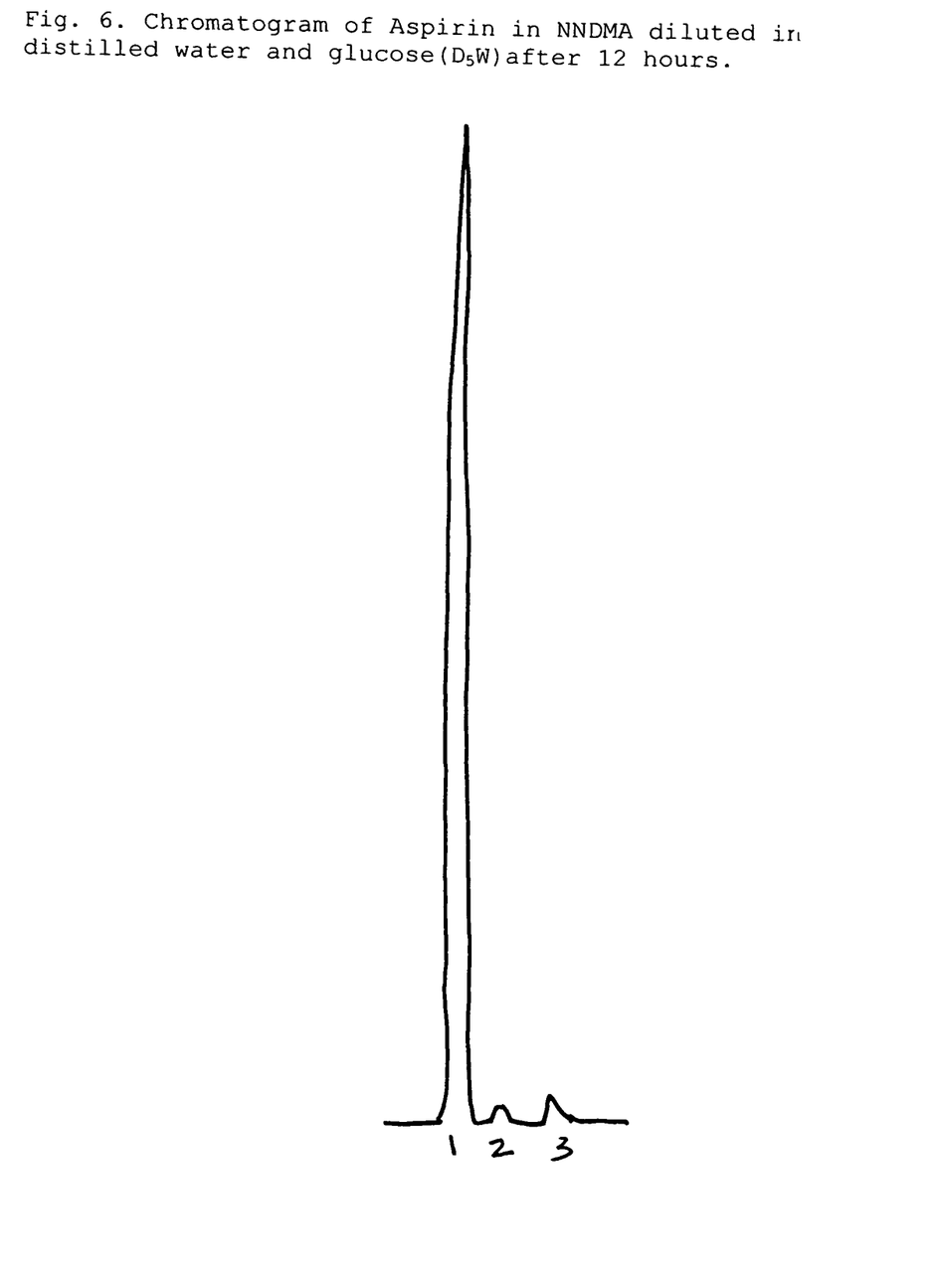
FIG. 6. HPLC chromatogram of aspirin in 1 ml solution of NNDMA diluted in distilled water and glucose ($D_5W$) after 12 hours. Peak 1 represents aspirin at 95% purity RT 1.8, peak 2, 0.3% RT 2.44 and peak 3 0.4% at RT 2.54. Minimal hydrolysis occurs over 12 hours with the aspirin product.

Solution Compatibility Experiments:

In another series of experiments, 1 ml of the solution containing only NNDMA (Table 3) was diluted with 100 ml of diluents such as 1. distilled $H_2O$, 2. Ringers lactate solution, 3. $D_5W$ and 4. normal saline and then the pH of these solutions were adjusted to 6.5 with 1 N NaOH. These solutions remained clear after a period of several days. HPLC indicated that up to 12 hours of storage, hydrolysis was found to be negligible (<1%). After 12 hours of storage, however, the hydrolysis of ASA was observed (up to 5% within 24 hours). Results of the HPLC analysis of the NNDMA and ASA solutions are reported in Table 4. FIG. 6 shows the HPLC results of the NNDMA solution of ASA showing that aspirin was present at a purity of 94.8%). One skilled in the art will recognize that modifications may be made in the persent invention without deviating from the spirit or scope of this invention which is illustrated further by the specific examples of dissolution attempts described herein and these examples are not to be construed as limiting the scope of this invention.

EXAMPLE 1

The Preparation of NNDMA Formulation of ASA and the Resultant HPLC Analysis

To 1.0 gm of aspirin is added a volume of 2 mL of N,N,-Dimethylacetamide and the mixture is stirred till a clear solution is obtained. A 10 µl solution of this formulation is tested using the following HPLC procedure for analysis. A constant-flow pump, Thermo-Finnigan Spectra-System P2000 was used to deliver eluent solvent at a rate of 1 ml/min to a column, Luna, 5µ, C8(2), 100 A, 100×46 mm (Phenomenex, Calif.). The eluent solvent system was $NaH_2PO4$ (0.025 M): $Na_2HPO4$ (0.25 M): MeOH (25:25:50 V/V) pH adjusted to 3.2 with either phosphoric acid or concentrated HCL. Methanolic solutions of aspirin and salicylic acid 10 µl (concentration of 1 mg/ml) were injected onto the column. The eluted compounds were detected using a Spectra 200 programmable UV wavelength detector and Thermo-Finnigan Chrome Jet integrator. The wavelength of detector was either 254 or 230 min. Under these conditions, retention times for aspirin and hydrolysis product, salicylic acid was approximately 1.75 minutes and 3.34 minutes respectively. The identity of these compounds was determined by mass spectrometry and "spiking" with known compounds that resulted in identical retention times. These results show that a solution of ASA in NNDMA results in a solution of ASA that is stable and resists hydrolysis. Preserving Anti-Platelet Activity of Aspirin:

Hydrolysis of aspirin markedly reduces the anti-platelet activity of aspirin. (Roth G J, Majerus P W. The mechanism of the effect of aspirin on human platelets, I: acetylation of a particulare fraction protein. J Clin Invest. 1975;56:624-632). A study was undertaken to evaluate the effects of aqueous ASA and ASA dissolved in NNDMA to evaluate platelet function. Platelet function was evaluated ex vivo using the "Verify Now"® assay developed by Accumetrics (San Diego, Calif.) that employs a method that is based upon the principle that agonist (arachidonic acid) induced activated platelets bind to fibrinogen-coated polystyrene beads that agglutinate in whole-blood. Infrared light transmittance through the chamber increase as the agglutinated platelets and beads fall out of the solution and thus can be detected and quantified by the device.

The NNMDA formulation of ASA was contrasted to an aqueous (water) formulation freshly prepared. The percent of drug not hydrolyzed and hydrolyzed was determined by HPLC assay. After preparing the solutions of ASA, the material was evaluated immediately, after 24 hrs, at 1 month and at 6 months. The new formulation showed essentially to hydrolysis; 99.8% freshly prepared, 99% purity at one day 40° C. storage temperature, 99% purity at 1 month 20° C. and 99% purity at 6 months. The aqueous preparation slowed 97% purity freshly prepared, 70% purity at 1 day, 56% purity at 1 month and only 11% purity at 6 months all stored at 40° C. Additionally, the biologic, anti-platelet activity of these solutions were evaluated using the "Verify Now" platelet measurement system on ex vivo platelets. The aqueous formulation tested immediately on platelets showed a 26% inhibition of platelet aggregability. The solution stored for 1 month and 6 months at 40° C. showed no inhibition of platelets. The ASA solution in NNDMA showed an initial 37% inhibition in platelet aggregation, 37% at 1 month and 39% at 6 months all material stored at 40° C. These data conclusively show that ASA stored in NNDMA as a solution retains its anti-platelet action. ASA stored in water does not retain anti-platelet action over time.

TABLE 1

Dissolution of ASA in different buffers that did not yield a clear solution

| | Buffers | Buffer Concentration | |
|---|---|---|---|
| a. | Bis Tris | 0.05 M not soluble | 0.10 M not soluble |
| b. | CAPS | " | " |
| c. | TAPS | " | " |
| d. | HEPES | " | " |
| e. | AMPSO | " | " |
| f. | Sodium acetate Ph 6.5, 3.8 | | |
| g. | Tricine | " | " |
| h. | Bicine | " | " |
| i. | Saline (normal) | " | " |

TABLE 2

Dissolution of ASA in Buffers that resulted in substantial ASA hydrolysis

| | | | | HPLC Results | |
|---|---|---|---|---|---|
| a. | H$_2$O (2.0 ml) | 1-Propanol (0.5 ml) | Tween 20 (0.5 ml) | ~5% salicylic acid | ~95% aspirin |
| b. | " | 1-Propanol (0.5 ml) | Tween 40 | ~5% salicylic acid | " |
| c. | " | 1-Propanol (0.5 ml) | Tween 60 | ~5% salicylic acid | " |
| d. | " | 1-Propanol (0.5 ml) | Tween 80 | ~5% salicylic acid | " |
| e. | " | 1-Propanol (0.5 ml) | PEG 300 | ~5% salicylic acid | " |
| f. | " | 1-Propanol (0.5 ml) | PEG 400 | ~5% salicylic acid | " |
| g. | " | 1-Propanol (0.5 ml) | PEG 600 | ~5% salicylic acid | " |
| h. | " | 1-Propanol (0.5 ml) | Glycerol | ~5% salicylic acid | " |
| i. | H$_2$O (2 ml) | +DMSO (1-2%) | Tween 20 | ~5% salicylic acid | " |
| j. | " | +DMSO (1-2%) | Tween 40 | ~5% salicylic acid | " |
| k. | " | +DMSO (1-2%) | Tween 60 | ~5% salicylic acid | " |
| l. | " | +DMSO (1-2%) | Tween 80 | ~5% salicylic acid | " |
| m. | Glycerine (1 ml) | 1-Propanol (3 ml) | Tween 80 (0.2 ml) | ~5% salicylic acid | " |
| n. | Glycerine (1 ml) | 1,2 propanediol (3 ml) | Tween 80 (0.2 ml) | ~5% salicylic acid | " |
| o. | Glycerine (1 ml) | PEG 300 (3 ml) | Tween 80 (0.2 ml) | ~5% salicylic acid | " |
| p. | Glycerine (1 ml) | PEG 400 (3 ml) | Tween 80 (0.2 ml) | ~5% salicylic acid | " |
| q. | Glycerine (1 ml) | PEG 600 (3 ml) | Tween 80 (0.2 ml) | ~5% salicylic acid | " |

TABLE 3

Dissolution of ASA in NNDMA and Other Diluents

| | Diluent | Diluent | Diluent | Results |
|---|---|---|---|---|
| 1. | N,N-Dimethylactamide (NNDMA) | — | — | Clear Purity >99% |
| 2. | N,N-Dimethylactamide (NNDMA) | Glycerol (0.1 in 10 ml) | Tween 20 (0.1 in 10 ml) | Clear solution Purity >99% |
| 3. | N,N-Dimethylactamide (NNDMA) | " | Tween 40 (0.1 in 10 ml) | Clear solution Purity >99% |

TABLE 3-continued

Dissolution of ASA in NNDMA and Other Diluents

| | Diluent | Diluent | Diluent | Results |
|---|---|---|---|---|
| 4. | N,N-Dimethylactamide (NNDMA) | " | Tween 60 (0.1 in 10 ml) | Clear solution Purity >99% |
| 5. | N,N-Dimethylactamide (NNDMA) | " | Tween 80 (0.1 in 10 ml) | Clear solution Purity >99% |
| 6. | N,N-Dimethylactamide (NNDMA) | Glycerol (0.1 in 10 ml) | | Clear solution Purity >99% |
| 7. | N,N-Dimethylactamide (NNDMA) | " | DMSO (1-2%) | Clear solution Purity >99% |
| 8. | N,N-Dimethylactamide (NNDMA) | DMSO (1.2%) | — | Clear solution Purity >99% |

TABLE 4

Stability of ASA in the presence of NNDMA

| Storage Conditions | Time for Storage | Aspirin | Salicylic Acid |
|---|---|---|---|
| RT | 6 months | >99% | <1% |
| 40° C. | 6 months | 97.9%-98.6% | Max. ~2% |

TABLE 5

The Dilution of ASA in NNDMA with D$_5$W at RT for 24 hours

| Storage Conditions | Time for Storage | Aspirin | Assay of Compounds Salicylic Acid |
|---|---|---|---|
| RT | Up to 12 hours | >99% | <1% |
| RT | Up to 24 hours | 94.7-95.3% | Max. ~6% |

What is claimed is:

1. A solution suitable for the preparation of a parenteral aspirin solution, comprising:
   10-500 mg/mL aspirin dissolved in N,N-dimethylacetamide (NNDMA),
   1% by volume glycerol,
   and 1% by volume polyoxyethylene (20) sorbitan monolaurate,
   wherein the pH of the solution is from 1.5-6.8.

2. A solution suitable for the preparation of a parenteral aspirin solution, comprising:
   10-500 mg/mL aspirin dissolved in N,N-dimethylacetamide (NNDMA),
   1% by volume glycerol,
   and 1% by volume polyoxyethylene (20) sorbitan monopalmitate,
   wherein the pH of the solution is from 1.5-6.8.

3. A solution suitable for the preparation of a parenteral aspirin solution, comprising:
   10-500 mg/mL aspirin dissolved in N,N-dimethylacetamide (NNDMA),
   1% by volume glycerol,
   and 1% by volume polyoxyethylene (20) sorbitan monostearate,
   wherein the pH of the solution is from 1.5-6.8.

4. A solution suitable for the preparation of a parenteral aspirin solution, comprising:
   10-500 mg/mL aspirin dissolved in N,N-dimethylacetamide (NNDMA),
   1% by volume glycerol,
   and 1% by volume polyoxyethylene (20) sorbitan monooleate,
   wherein the pH of the solution is from 1.5-6.8.

5. A solution suitable for the preparation of a parenteral aspirin solution, comprising: 10-500 mg/mL aspirin dissolved in N,N-dimethylacetamide (NNDMA) and from 1-2% by volume DMSO.

6. A solution suitable for the preparation of a parenteral aspirin solution, comprising:
   10-500 mg/mL aspirin dissolved in N,N-dimethylacetamide (NNDMA),
   1% by volume glycerol,
   and from 1-2% by volume DMSO,
   wherein the pH of the solution is from 1.5-6.8.

7. An aspirin solution, comprising: 10-500 mg/mL aspirin, 1% by volume N,N-dimethylacetamide (NNDMA), and 99% by volume of solvent being selected from the group consisting of:
   a. distilled H$_2$O,
   b. Ringers lactate solution,
   c. 5% dextrose solution (D$_5$W), and
   d. saline solution,
wherein the pH is 6.5 and the solution is suitable for parenteral administration.

* * * * *